United States Patent
Wang et al.

(10) Patent No.: US 7,410,658 B2
(45) Date of Patent: Aug. 12, 2008

(54) **USE OF *ALISMA ORIENTALE* IN COSMETICS AND COMPOSITIONS THEREOF**

(75) Inventors: Helen H. Wang, Suffern, NY (US); Michelle D. Hines, Lawnside, NJ (US)

(73) Assignee: Avon Products, Inc., New York, NY (US)

( * ) Notice: Subject to any disclaimer, the term of this patent is extended or adjusted under 35 U.S.C. 154(b) by 327 days.

(21) Appl. No.: 11/021,023

(22) Filed: Dec. 22, 2004

(65) Prior Publication Data

US 2006/0134246 A1 Jun. 22, 2006

(51) Int. Cl.
*A61K 36/00* (2006.01)
(52) U.S. Cl. ............................ 424/725; 424/773
(58) Field of Classification Search .............. None
See application file for complete search history.

(56) References Cited

U.S. PATENT DOCUMENTS

| | | | |
|---|---|---|---|
| 4,379,454 A | 4/1983 | Campbell et al. | |
| 4,820,724 A | 4/1989 | Nimni | |
| 4,956,171 A | 9/1990 | Chang | |
| 5,146,846 A | 9/1992 | Lee et al. | |
| 5,223,262 A | 6/1993 | Kim et al. | |
| 5,595,743 A * | 1/1997 | Wu | 424/728 |
| 5,770,222 A | 6/1998 | Unger et al. | |
| 5,834,513 A | 11/1998 | Ptchelintsev et al. | |
| 5,847,003 A | 12/1998 | Ptchelintsev et al. | |
| 6,790,464 B2 * | 9/2004 | Kuok et al. | 424/725 |
| 6,933,291 B2 * | 8/2005 | Qi et al. | 514/171 |
| 2002/0031559 A1 * | 3/2002 | Liang et al. | 424/725 |
| 2004/0247654 A1 * | 12/2004 | Asmus et al. | 424/449 |
| 2005/0142231 A1 * | 6/2005 | Gong et al. | 424/762 |
| 2006/0018867 A1 * | 1/2006 | Kawasaki et al. | 424/70.122 |

FOREIGN PATENT DOCUMENTS

| | | | |
|---|---|---|---|
| CN | 1104479 | * | 7/1995 |
| CN | 1105557 | * | 7/1995 |
| CN | 1267472 | * | 9/2000 |
| CN | 1286924 | * | 3/2001 |
| JP | 09087187 | * | 3/1997 |
| JP | 10045613 | * | 2/1998 |
| JP | 2004-035442 | | 2/2004 |
| JP | 2004035442 | * | 2/2004 |
| WO | WO 01/66067 | | 9/2001 |

OTHER PUBLICATIONS

Nedvidkova J, et al. "Adiponectin, an adipocyte-derived protein" Physiol Res., Nov. 15, 2004.
Gil-Campos M M, et al. "Adiponectin, the missing link in insulin resistance and obesity" Clin Nutr. 23(5):963-74, 2004.
Putz DM, et al. "Adiponectin and C-reactive protein in obesity, type 2 diabetes, and monodrug therapy" Metabolism 53(11):1454-61, 2004.
Shetty GK, et al. Circulating adiponectin and resistin levels in relation to metabolic factors, inflammatory markers, . . . Diabetes Care. 27(10):2450-7,2004.
Schulze MB, et al. "Relationship between adiponectin and glycemic control, blood lipids, and inflammatory markers in men with type 2 diabetes" Diabetes Care. 27(7):1680-7,2004.
Meier U & Gressner AM. "Endocrine regulation of energy metabolism: review of pathobiochemical and clinical chemical aspects . . ." Clin Chem. 50(9):1511-25, 2004.

* cited by examiner

*Primary Examiner*—Christopher R. Tate
(74) *Attorney, Agent, or Firm*—Joan M. McGillycuddy; Charles J. Zeller; Anthony M. Santini

(57) ABSTRACT

The present invention describes compositions and methods for improving the appearance of skin, particularly, treating, preventing, ameliorating, reducing and/or eliminating excess accumulation or production of subcutaneous fat, such as cellulite, or conditions related to excess accumulation, production, or excretion of sebum, such as acne, an oily complexion, oily hair or scalp, or undesirable body odor, by topically applying compositions comprising *Alisma orientate* constituents, or extracts therefrom.

7 Claims, No Drawings

USE OF *ALISMA ORIENTALE* IN COSMETICS AND COMPOSITIONS THEREOF

FIELD OF THE INVENTION

This invention generally relates to cosmetic compositions and their use, and more particularly to cosmetic compositions and to their use in improving the condition and appearance of skin or hair.

BACKGROUND OF THE INVENTION

Active ingredients or components derived from plants and plant seeds have commonly been employed for a myriad of medicinal, therapeutic and cosmetic purposes. Such actives may be obtained from the entire plant or various parts of a plant, such as seeds, needles, leaves, roots, bark, cones, stems, rhizomes, callus cells, protoplasts, organs and organ systems, and meristems. Active ingredients or components are incorporated in compositions in a variety of forms. Such forms include a pure or semi-pure component, a solid or liquid extract or derivative, or a solid natural plant material. Plant material may be incorporated in a variety of subforms such as whole, minced, ground or crushed.

A problem commonly encountered when using an active agent, ingredient, or component derived from a natural plant material and/or plant seed is the relatively low level at which they are naturally present. Such low levels frequently require relatively large amounts of the natural plant material be processed in order to obtain desired or useful quantities of actives. For rare plants or plant seeds, such large amounts may be unavailable or difficult to obtain.

There is active interest in the cosmetics industry to develop products that may be applied topically to the skin that provide anti-acne, anti-oil, and anti-cellulite benefits. Cosmetic products that enhance the appearance of skin are increasingly in demand. Consumers are interested in mitigating or delaying the signs of excess sebum accumulation, production or excretion and excess accumulation or production of subcutaneous fat. During the teenage years, the complexion of the skin, i.e., the color and appearance of the skin, is oily due primarily to hormonal changes.

Sebum is an oily secretion containing fat, keratin, and cellular material, produced by sebaceous glands, which are tiny ducts adjacent to hair follicles. Sebum is secreted into the skin and hair. Both excess and lack of sebum are undesirable. Excess sebum is associated with oily skin or hair and acne. It is particularly common in adolescents as the increased levels of sex hormones stimulate sebum production. Cosmetic products that are able to provide anti-acne, anti-oil, and anti-cellulite benefits are highly desirable, to both manufacturers and consumers.

In traditional Chinese medicine, *Alisma orientale* has been used as an herbal medicine to eliminate extra water and heat from the body, improve kidney function, enhance blood circulation, increase metabolism, and to decrease the levels of blood glucose, lipids and cholesterol. A water plantain in the *Alisma* genus and Alismataceae family having a Latin botanical name of *Alisma orientale* (Sam.) Juzep.(a plantago-aquatica L. var. orientale Sam.) (a.k.a. "*Alisma orientate*," "Ze Xie," "Fu Ze Xie," or "Jiang Ze Xie" (Chinese names) or "*Rhizoma alismatis*" (medical name)) is commonly found in Europe, Africa, East Asia, for example China, and North America.

A topical cosmetic composition having an active ingredient, agent, or component derived from a natural plant material, or extract therefrom, is desired in the treatment, prevention, control, amelioration, inhibition and/or reduction of signs of excess sebum accumulation, production, or excretion, including oily, shiny, or acne prone skin, oily hair, oily scalp, or undesirable body odors, and increased subcutaneous fats or cellulite.

Excess sebum production is a common problem particularly with teenagers leading to an oily or shiny appearance of the skin which is one of the principal factors causing acne. Sebum is a semi-fluid secretion of the sebaceous glands, comprising primarily of fat, keratin, and cellular material. The oily/shiny appearance of skin results from excess sebum excretion in the sebaceous glands. Additionally, odors may be emitted as a result of excess sebum accumulation, production, or excretion. The classic approach to addressing oily or shiny skin is the use of powders that provide an immediate masking effect by absorbing the excess sebum on the skins surface. Such an approach has short term benefit only and has a minimal effect on conditions such as acne caused through excess sebum production.

Cellulite is the lumpy uneven type of fat that is subcutaneous and accumulates primarily on the buttocks, thighs, and limbs of many women. It is rather unsightly because it gives the tissues underlying the skin an 'orange peel' or 'cottage cheese' look. Pinching of the skin produces a 'mattress appearance' with bulging and pitting of the fatty layer. One may be able to feel tender nodules of fat trapped inside hardened connective tissue. A number of factors can cause cellulite including, hereditary, intestinal, circulatory, lymphatic, hormonal, and lifestyle factors. Dieting to decrease additional fat intake, exercise to increase fat metabolism and prevent the build up of cellulite, and massage and/or hydrotherapy may help to stimulate lymphatic drainage and reduce cellulite. However, all of these means for reducing cellulite or subcutaneous fat are limited, producing little visible results over extended periods of time.

Therefore, safe, effective, natural, and new components of compositions to treat, prevent, reduce, inhibit, and/or improve the signs of excess accumulation, production, or excretion of sebum and subcutaneous fat would be advantageous for the formulation of treatments and products for the skin or hair. As described herein, novel and beneficial methods and compositions, as well as their mode of action, for the treatment of conditions related to excess accumulation, production, or excretion of sebum and subcutaneous fat, and the like, for skin and hair formulations, as well as, personal care products for the skin, are provided by the present invention.

SUMMARY OF THE INVENTION

It is an object of the present invention to provide a topical cosmetic composition that delivers an effective level of an active ingredient from a natural plant material (extract, ingredient, or constituent).

It is another object of the present invention to provide topical cosmetic compositions having a natural plant ingredient or blends of natural plant ingredients in a cosmetically, dermatologically, physiologically, or pharmaceutically acceptable vehicle, carrier, or diluent.

It is a further object of the present invention to provide topical compositions having lipolysis-stimulating active ingredients in a pharmaceutically, physiologically, dermatologically, or cosmetically acceptable vehicle, carrier, or diluent.

It is still another object of the present invention to provide a topical composition that delivers active ingredients derived from a plant, or extract therefrom, in an amount sufficient to stimulate lipolysis and inhibit PPAR-gamma upregulation, stearoyl CoA desaturase upregulation, and adiponectin production.

It is yet another object of the invention to provide a topical composition having extract isolated from the *Alisma orientale* plant to treat, prevent, control, ameliorate, inhibit, and/or reduce signs of excess sebum accumulation, production, or excretion, including oily, shiny, or acne prone skin, oily hair, oily scalp, or undesirable body odors, and increased subcutaneous fat or cellulite, thereby improving the aesthetic appearance of conditions relating to skin, including but not limited to skin, hair, and undesirable body odors.

It is still a further object of the present invention to provide a method for topically applying such compositions to the skin. As hair is derived from skin, methods and compositions of the present invention also relate to hair.

It is an object of the present invention to provide a method for delivering a consistent level of an active ingredient to skin by topically applying a composition having one or more natural plant active agents, ingredients, or constituents.

These and other objects and advantages of the present invention, and equivalents thereof, are achieved by cosmetic compositions having a single natural botanical ingredient or blends of natural botanical ingredients, and use of such compositions for topical application.

DETAILED DESCRIPTION OF THE INVENTION

The present invention relates to topical compositions having a natural plant material (extract, ingredient, or constituent), or an active agent or component derived therefrom. More particularly, the present invention relates to topical compositions that improve the condition and aesthetic appearance of skin, including but not limited to, hair or odors associated with excess sebum production from skin pores. Still more particularly, the present invention relates to methods of using the topical composition not only for improving the aesthetic appearance of conditions related to skin, such as reducing cellulite and excess accumulation or production of subcutaneous fat and treating acne-, oil-, or shiny-prone skin and oily hair conditions, but also to inhibit or reduce undesirable odors associated with the release of fats.

It is to be understood that references made to skin also include hair. Hair itself is dead, but it is produced by living cells. Those cells are epidermal in nature and origin, and the hair, like the other adnexa of the skin, is epidermal in nature. The hair is also prone to oil from excess sebum accumulation, production, or excretion. Therefore, the compositions of the invention are also useful in preventing, reducing, and ameliorating oily hair.

The present invention relates to the novel use of *Alisma orientate* plants, or extracts therefrom, in cosmetic products for the face, hair, and/or body. More particularly, the present invention relates to the use of topical compositions having a natural plant material, or extract derived therefrom, to treat, prevent, ameliorate, and/or reduce, signs of excess sebum production, and/or improve the aesthetic appearance of conditions relating to skin, where the plant component stimulates lipolysis and/or inhibits PPAR-gamma upregulation, stearoyl CoA desaturase upregulation, or adiponectin production. The plant component may be from the Alismataceae family, particularly, *Alisma orientate* (Sam.) Juzep., *Alisma plantago-aquatica* var. *orientate*, or *Alisma orientate*, also known as, Ze Xie, *Alisma, Alismatis Rhizoma*, Greater Thrumwort, Mad-Dog Weed, Mud Plantain, Tse Hsieh, or Water Plantain.

The component(s) of these plants which reduce subcutaneous fat by lipolysis are effective when applied topically, and, without wishing to be bound by theory, lipids are broken down by the active ingredients in the composition comprising the *Alisma orientale* plant, or extract therefrom. Topical application of the *Alisma orientale* plant components also facilitates the targeted delivery of the active components without the requirement of an injection or the expertise of a health practitioner.

The present invention, therefore, provides novel compositions and methods using components of an *Alisma orientale* extract, which are newly found to be effective to treat, prevent, ameliorate, and/or reduce, signs of excess sebum production or excess accumulation or production of subcutaneous fat, and/or improve the aesthetic appearance of conditions related to skin, hair or undesirable body odors, upon daily application.

Compositions Comprising *Alisma orientale* Plants

For purposes of the invention, the *Alisma orientale* plant may be in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, an extract, a dried extract, a synthetic extract, or components and/or constituents found in, or isolated from, the plant, and/or portions of the plant, or extracts derived either directly or synthetically from the plant, or any combinations thereof.

In one embodiment, the topical compositions of the invention are useful for improving the aesthetic appearance of conditions related to skin, particularly teenage skin, by any one of the following methods:

1. Reducing oil production by sebaceous glands;
2. Reducing lipid synthesis in subcutaneous adipose tissue;
3. Reducing triglyceride synthesis in subcutaneous adipose tissue;
4. Preventing and/or improving conditions related to skin associated with inducing lipolysis;
5. Preventing and/or improving conditions related to skin associated with nonselective or partially selective PPAR receptor stimulators/upregulators;
6. Preventing and/or improving conditions related to skin associated with stearoyl CoA desaturase activity;
7. Preventing and/or improving conditions related to skin associated with adiponectin production;
8. Preventing, ameliorating or treating acne;
9. Preventing, ameliorating or treating oily skin;
10. Preventing, ameliorating or treating oily hair;
11. Preventing, ameliorating or treating oily scalp;
12. Preventing, ameliorating or treating blemishes; and
13. Preventing, ameliorating or treating skin eruptions or "breakouts";
14. Preventing, ameliorating or treating body odors associated with excess sebum production;
15. Preventing, ameliorating or treating cellulite in adults;
16. Preventing, ameliorating or treating excess accumulation or production of subcutaneous fat in adults; and
17. Improving skin texture.

The composition may have an *Alisma orientale* extract in an amount from about 0.0001% to about 50%, preferably from about 0.001% to about 20%, more preferably from about 0.01% to about 2%, and most preferably from about 0.05% to about 1%, based on the total weight of the composition.

In another embodiment, the *Alisma orientale* plant extract as used herein, also includes "synthetic" extracts, i.e. various combinations of known *Alisma orientale* plant components and/or constituents that are combined to substantially mimic the composition and/or activity of an *Alisma orientale* plant extract of natural origin. Such synthetic extracts are included in the term "*Alisma orientale* plant extract." Most preferably, the synthetic extracts will have substantially the same number of active ingredients as a natural extract. The correspondence of the numerical incidence of active ingredients between the synthetic extracts and the plant or a natural extract may also be described in terms of "percent commonality."

Another embodiment relates to a synthetic extract having about 50% or more commonality to the chemical composition of a plant or natural extract. For example, the synthetic extract has about 50% or more of the active ingredients found in the plant or a natural extract. The chemical composition of the synthetic extract may have about 70% or more commonality to the chemical composition of a plant or a natural extract. A synthetic extract may have about 90% or more commonality to the chemical composition of a plant or a natural extract. The plant or natural extract for comparison is derived, most preferably, from the *Alisma orientale* plant.

For use in the compositions of the invention, the plant raw material and/or active constituents are preferably derived directly from the *Alisma orientale* plant, including the seeds, needles, leaves, roots, bark, cones, stems, rhizomes, callus cells, protoplasts, organs and organ systems, and meristems. The components may be in a pure form, a semi-pure form, or unpurified form. In one embodiment, the components are in the form of an extract obtained by extracting the rhizome of *Alisma orientalis Juzep* with a 50% water/50% ethanol solution (Example 1).

Briefly, the organic solvent extraction method involves washing and extracting the plant material using an organic solvent. Non-limiting examples of organic solvents include methanol, ethanol, isopropanol, dichloromethane, chloroform, hexane, xylene, and petroleum ether. An extracting machine may be used for organic solvent extraction as is well known in the field.

Organic solvent extraction involves collecting the raw materials from the plant that contain the desired constituent(s), such as seeds, needles, leaves, roots, bark, cones, stems, rhizomes, callus cells, protoplasts, organs and organ systems, and meristems. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time between about 1-8 hours is suitable, and more preferably is between about 2-6 hours, and most preferably is between about 3-5 hours. The temperature of extraction is between about 30° C.-90° C., preferably between about 40° C.-70° C., and more preferably between about 50° C.-60° C. The collected extract is then fine-filtered to remove debris, and may be used directly, or is concentrated, for example by distilling the solvent or by other conventional processing, and may be provided in powder form.

Similarly, aqueous-organic solvent extraction involves initially collecting raw materials from a plant containing the desired alkaloid(s), such as seeds, needles, leaves, roots, bark, cones, stems, rhizomes, callus cells, protoplasts, organs and organ systems, and meristems of the plant, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated or dried. Alternatively, organic solvent may then be added to the neutralized solution to transfer the extract actives from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction may preferably be used for extracting those plants containing constituents having similar solubility in the solvent used for extraction, such as ethanol. The mixture of extracts may be concentrated and stored in an appropriate solvent.

Formulations

In accordance with the invention, compositions comprising components from the *Alisma orientale* plant include, but are not limited to, topically applied formulations, anti-oxidants, anti-inflammatories, sunscreens, cosmetics, including makeup, formulations for reducing excess subcutaneous fats, e.g., anti-cellulite creams, or excess sebum production formulations for treating oily skin or hair, blemishes, or acne, personal care products, e.g., anti-perspirants or deodorants, topicals, skin penetration enhancers, and the like. Also in accordance with this invention, the *Alisma orientale* plant components and additional ingredients comprising such compositions may be formulated in a variety of product forms. The compositions may be prepared in targeted delivery systems, e.g. creams, lotions, gels, toners, serums, transdermal patches, and the like, particularly for topical administration. Targeted delivery and/or penetration enhancement may also be achieved by iontophoresis.

The present invention further provides the compositions comprising the *Alisma orientale* plant components preferably for topical administration or for targeted delivery. The inventive compositions are suitable for all skin types, such as sensitive, normal, or oily. In particular embodiments, the compositions may be preferably for oily skin or hair types. The compositions are applied to the skin or hair for a period of time sufficient to improve the aesthetic appearance of conditions related to skin, including signs of excess sebum production, e.g., oily skin or hair, acne, body odors, and/or subcutaneous fats, e.g., cellulite. The compositions may be applied topically once, twice, or more daily, preferably once a day. The daily application may be applied for a period of one week, two weeks, four weeks, or more.

The compositions may be formulated into liposomes which can comprise other additives or substances, and/or which can be modified to more specifically reach or remain at a site following administration. The compositions of the present invention yield improvements to the aesthetic appearance of conditions related to skin by treating at least one of the following: excess sebum production, including oily skin or hair, conditions related to acne, conditions related to body odors, and cellulite or excess subcutaneous fats.

Another embodiment of the invention encompasses compositions comprising a cosmetically or dermatologically acceptable formulation which is suitable for contact with living animal tissue, including human tissue, with virtually no adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions of this invention include, for example, an emulsion, a cream, a balm, a gloss, a lotion, a mask, a serum, a toner, an ointment, a mousse, a patch, a pomade, a solution, a spray, a wax-based stick, or a towelette. In addition, the compositions contemplated by this invention can include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition," incorporated herewith) and the like, as well as other botanicals such as aloe, chamomile, and the like, and as further described below.

Also, embraced by the invention are transdermal modes of delivery, such as patches and the like, with or without a suitable penetration enhancers. The methods and compositions embodied by the invention provide a means by which the *Alisma orientale* components can be effectively administered in a transdermal system. Accordingly, a transdermal means of delivering a composition or formulation (often with a penetration enhancing composition) to the skin is that of the transdermal patch or a similar device as known and described in the art. Examples of such devices are disclosed in U.S. Pat. Nos. 5,146,846; 5,223,262; 4,820,724; 4,379,454; and 4,956,171, all of which are incorporated herein by reference and such descriptions are not meant to be limiting. The transdermal mode of storing and delivering the compositions onto the skin, including hair, and forming the active composition is convenient and well-suited for the purposes of an embodiment of the present invention. In a preferred method, the application is through a sustained release vehicle, carrier, or diluent, e.g., a topically applied sustained released patch. Preferably, when a topical patch is used, the patch is applied to the desired area for extended period of time. Preferably, the extended period of time is greater than one hour, most preferably the extended period of time is overnight, i.e., when the user is sleeping.

The *Alisma orientale* plant component(s) of the present invention are preferably contained in a cosmetically or dematologically acceptable vehicle, medium, diluent or carrier, for use in treating, reducing, ameliorating, or preventing conditions associated with excess accumulation, production, or excretion of sebum and excess accumulation or production of subcutaneous fat.

In an embodiment embracing topical application, the compositions of this invention comprise a medium (vehicle, diluent or carrier) that is compatible with human skin, including hair. The compositions can be formulated as an aqueous phase, an oil phase, alcohol, or aqueous/alcohol-based solutions, ointments, lotions, gels, a wax-in-water emulsion, or water-in-oil, oil-in-water, of water-oil-water triple emulsions having the appearance of a cream or gel, microemulsions, or aerosols.

The aqueous phase is a mixture of one or more water soluble or water dispersible ingredient, which can be liquid, semi-solid or solid at room temperature (25° C.). The vehicle comprises or can be in the form of a suspension, dispersion or solution in water or an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In one embodiment, the composition may include an aqueous phase which may contain water or a mixture of water and at least one hydrophilic organic solvent in particular an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 weight % to about 99.99 weight %, based upon the total weight of the composition.

Yet another embodiment when the composition of the invention is in the form of an emulsion, the composition may also optionally comprise a surfactant, preferably in an amount of from about 0.1 weight % to about 30 weight %, and in particular, from about 1 weight % to about 20 weight %, based upon the total weight of the composition.

In a further embodiment of the invention, the composition may also comprise a thickening polymer such as an amphiphilic polyurethane, a polyacrylic homopolymer or copolymer, a polyester, and/or a hydrocarbon-based resin.

One embodiment of the invention further relates to a composition of the invention which may also comprise an oil phase containing oil soluble or oil dispersible ingredients that are liquid at room temperature (25° C.) and/or oily or waxy substances that are solid at room temperature, such as waxes, semi-solids, gums, and mixtures thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polydimethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, preferably from about 1 weight % to about 80 weight % by weight of the oil phase.

The oil phase of the composition of the invention may also comprise one or more cosmetically acceptable organic solvents. These solvents are present in an amount of about 0 weight % to about 60 weight %, preferably about 1 weight % to about 30 weight %, based on the total weight of the composition, and may be selected from the group consisting of lipophilic organic solvents, amphiphilic organic solvents and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof.

The composition of the invention may further comprise any ingredient conventionally used in the cosmetics field. These ingredients include preserving agents, aqueous phase thickeners (polysaccharide biopolymers, synthetic polymers) and fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition. The nature of these ingredients and their amounts must be compatible with the production of the compositions of the invention.

The composition of the invention may also comprise an additional particulate phase, typically present in an amount of about 0 weight % to about 30 weight %, based upon the total weight of the composition, preferably from about 0.05 weight % to about 20 weight %, and which can comprise pigments and/or pearlescent agents and/or fillers used in cosmetic compositions.

Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment. Fillers are normally present in an amount of about 0 weight % to about 20 weight %, based on the total weight of the composition, preferably about 0.1 weight % to about 10 weight %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Coming), and silicone resin microbeads (Tospearl from Toshiba).

The oil phase of the compositions of the invention may comprise one or more waxes, gums, or mixtures thereof. The waxes include hydrocarbon-based waxes, fluoro waxes and/or silicone waxes and can be of plant, mineral, animal and/or synthetic origin. The compositions of the present invention may contain from about 0 weight % to about 20 weight % waxes, based upon the total weight of the composition. The gums are generally high molecular weight PDMSs, cellulose gums or polysaccharides, and the semi-solid materials are generally hydrocarbon-based compounds, such as, but not limited to, lanolins and derivatives thereof, or alternatively PDMSs In addition, the compositions can be in the form of vesicular dispersions containing ionic and/or nonionic lipids, as described above. Dosage units suitable for such compositions are formulated according to the conventional knowledge and techniques used in the art.

More particularly, the compositions for topical application can be in the form of a protective care composition for the skin, preferably for the face, the neck, the hands, the feet, or other areas of the body. Non-limiting examples include day creams or lotions, night creams or lotions, salves, sunscreen creams, fluid lotions, oils, ointments, gels, masks, body milks, makeup (a foundation), artificial tanning compositions, depilatories, emulsifiers, patches, or a solid which is poured or cast as a stick or a dish, for example.

Another particular embodiment of the present invention is directed to the delivery of the described compositions by the use of targeted delivery systems, for example, liposomes, microspheres (see, e.g., U.S. Pat. No. 5,770,222 to Unger et al., incorporated herein by reference), and the like, so that the *Alisma orientale* compositions and/or active constituents can more readily reach and affect the muscle layer of the area of application, e.g., face or neck, or the other area of the skin.

In another embodiment, the topical compositions of the present invention may also include one or more of the following: a skin penetration enhancer, an emollient, a skin plumper, an optical diffuser, a sunscreen, an exfoliation promoter, and an antioxidant. Details with respect to these and other suitable cosmetic ingredients can be found in the International Cosmetic Ingredient Dictionary and Handbook, 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient is preferably present from about 0.1 wt % to about 50 wt% of the total weight of the composition.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 wt % to about 20 wt% of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 wt % to about 20 wt% of the total weight of the composition.

A sunscreen protects the skin from damaging ultraviolet rays. In an illustrative embodiment of the invention, the sunscreen would provide both UVA and UVB protection, by using either a single sunscreen or a combination of sunscreens. Among the sunscreens that can be employed in the present compositions are avobenzone, cinnamic acid derivatives (such as octylmethoxy cinnamate), octyl salicylate, oxybenzone, titanium dioxide, zinc oxide, or any mixtures thereof. The sunscreen may be present from about 1 wt % to about 30 wt% of the total weight of the composition. The addition of a sunscreen may protect the skin from ultraviolet radiation.

The compositions of the invention having sunscreen bring about additional improvements to the aesthetic appearance of skin, including at least one of the following: minimizes sunburning, minimizes tanning, and reduces redness.

In an embodiment of the invention, compositions may also have one or more exfoliation promoters. Suitable examples of an exfoliation promoter that can be used in the present compositions include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. (See also, Dictionary at p. 2205).

When an embodiment of the invention includes an exfoliation promoter, the composition has about 0.1 wt % to 30 wt%, preferably about 1 wt% to about 15 wt% and more preferably about 1 wt% to about 10 wt%, of the exfoliation promoter based on the total weight of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 wt % to about 10 wt%, and more preferably from about 0.01 wt% to about 5 wt%, of the total weight of the composition. See also, Dictionary at p. 2184.

In an embodiment of the invention, the composition may also have one or more of the following cosmetic and pharmaceutical active agents, excipients, ingredients, or adjuvants: anesthetics, antibiotics, e.g., erythromycins and tetracyclines, salicylic acids, anti-allergenics, antifungals, antiseptics, anti-irritants, anti-inflammatory agents, antimicrobials, analgesics, nitric oxide synthase inhibitors, insect repellents, self-tanning agents, skin penetration enhancers, skin cooling agents, chelating agents, colorants including dyes, lakes and pigments that may be untreated or chemically surface treated to improve wetability or some other property, demulcents, emollients, emulsifiers, fragrances, humectants, lubricants, skin protectants, moisturizers, pH adjusters, preservatives, stabilizers, surfactants, thickeners, film formers, plasticizers, viscosity modifiers, vitamins, or any mixtures thereof. The amounts of these various substances are those that are conventionally used in the cosmetic or pharmaceutical fields to achieve their intended purposes, for example, they may constitute from about 0.01% to 20% of the total weight of the composition.

Non-limiting examples of active agents for formulating into the compositions of the invention include those reagents having an effect on the treatment of wrinkles and/or fine lines, in addition to the *Alisma orientale* actives as described, such as keratolytic agents, i.e., an active agent having desquamating, exfoliant, or scrubbing properties, or an active agent which can soften the horny layer of the skin. Other examples of anti-wrinkle or anti-fine line active agents include hydroxy acids and retinoids. These agents can be formulated, for example, in amounts of from about 0.0001% to 5% by weight relative to the total weight of the composition.

Suitable hydroxy acids include, for example, glycolic acid, lactic acid, malic acid, tartaric acid, citric acid, 2-hydroxyalkanoic acid, mandelic acid, salicylic acid and alkyl derivatives thereof, including 5-n-octanoylsalicylic acid, 5-n-dodecanoylsalicylic acid, 5-n-decanoylsalicylic acid, 5-n-octylsalicylic acid, 5-n-heptyloxysalicylic acid, 4-n-heptyloxysalicylic acid and 2-hydroxy-3-methylbenzoic acid or alkoxy derivatives thereof, such as 2-hydroxy-3-methyoxybenzoic acid.

Emulsifiers are typically present in the compositions of the invention in an amount of about 0.01% to 30%, by weight and preferably from about 0.5% to 30% by weight relative to the total weight of the composition. However, not all compositions will necessarily include emulsifiers. (See e.g., Dictionary at p. 2276-2285).

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate. (See, e.g., Dictionary at p. 2293-2299).

The topical compositions of the present invention may include, and their utility can be enhanced by one or more humectants, such as ureas, pyrrolidone carboxylic acids, amino acids, sodium hyaluronates, certain polyols and other compounds with hygroscopic properties. (See Dictionary at p. 2244).

The general activity and mildness to skin of the present topical compositions can also be enhanced by neutralization to pH about 3.5 to about 7.0, most preferably from pH about 3.7 to about 5.6. This neutralization is preferably accomplished with one or more of ammonium hydroxide, potassium hydroxide, sodium hydroxide, arginine or other amino acids, and/or triethanolamine.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

The topical compositions of the present invention can be further formulated according to procedures known in the art to provide cosmetic compositions such as emulsions, gels, creams, lotions, conditioners, shampoos, anti-deodorants, anti-perspirants, ointments, pastes, sticks, cakes, pencils, essences, and serums, as well as other topical cosmetic vehicles. It is also contemplated that topical compositions of the present invention can be incorporated into delivery systems such as liposomes and topical patches, tapes, and sprays.

Methods of use of *Alisma orientale* Plants

In another embodiment, the present invention encompasses a method of improving the aesthetic appearance of conditions related to skin, including hair and body odors, comprising applying to skin and hair, a composition containing at least one component of an *Alisma orientale* plant. In a specific embodiment, the component is in an extract of *Alisma orientale* in a pharmaceutically, physiologically, cosmetically, and dermatologically -acceptable medium, and in an amount effective to treat, reduce, prevent, and/or ameliorate signs of excess sebum production, oily or shiny skin, acne-prone skin, oily hair, and body odors associate with excess sebum production, excess subcutaneous fats and cellulite. The composition containing an extract of *Alisma orientale* in medium preferably stimulates lipolysis, inhibits PPAR-gamma, stearoyl CoA desaturase, or adiponectin in order to treat, reduce, prevent, and/or ameliorate these conditions related to skin. The application of the *Alisma orientale* component containing composition is preferably topical.

One embodiment of the invention relates to methods of applying an effective amount of a plant, or plant extract therefrom, to induce lipolysis to affected areas of the skin or hair. Lipolysis is the process in which triglycerides are hydrolyzed into glycerol and free fatty acids. Lipolysis releases free fatty acids (FFA) into the bloodstream where they may be either re-esterified by the adipocyte or travel to other tissues and exert other effects throughout the body. The breakdown of triglycerides in adipocytes leads to release of free fatty acids and glycerol into the medium. The plant is preferably *Alisma orientale*, and more preferably an extract of *Alisma orientale* (Sam.) Juzep. The *Alisma orientale* plant, or extract therefrom, is useful as an inducer of lipolysis which can thereby treat or reduce conditions associated with excess sebum accumulation, production, or excretion, as well as subcutaneous fat, including cellulite.

In an embodiment of the foregoing methods, an effective amount of a PPAR upregulation inhibitor in a topical composition is applied to affected areas. Preferably, the PPAR upregulation inhibitor is an *Alisma orientale* plant or extract therefrom, more preferably, the extract is from a rhizome of the *Alisma orientale* (Sam.) Juzep plant. The peroxisome proliferator-activated receptor gamma (PPAR-gamma) structurally belongs to a superfamily of nuclear transcription factors and activation of this receptor has both physiological and pathological significance, particularly in the control of lipid metabolism and inflammatory response. Nuclear hormone receptors are ligand-dependent intracellular proteins that stimulate transcription of specific genes by binding to specific DNA sequences following activation by the appropriate ligand. PPAR-gamma activity is governed by binding of small lipophilic ligands, mainly fatty acids, derived from nutrition or metabolic pathways that are often controlled by PPAR-gamma. PPAR-gamma is purported to be the centerpiece of a feed-forward pathway that favors differentiation and energy storage by adipocytes. The *Alisma orientale* plant, or extract therefrom, is useful as a PPAR upregulation inhibitor which can thereby provide a positive effect on acne and cellulite.

One embodiment of the invention relates to methods of applying an effective amount of a plant, or plant extract therefrom, to inhibit stearoyl-CoA desaturase (SCD) to affected areas of the skin or hair. The plant is preferably *Alisma orientale*, and more preferably an extract of *Alisma orientale* (Sam.) Juzep. Lipid compositions of cellular membranes are regulated in order to maintain membrane fluidity. A key enzyme involved in this process is the membrane-bound stearoyl-CoA desaturase (SCD) which is the rate-limiting enzyme in the cellular synthesis of mono-unsaturated fatty acids from saturated fatty acids. A proper ratio of saturated to mono-unsaturated fatty acids contributes to membrane fluidity. Oleic acid and palmitoleic acid are the major monounsaturated fatty acids in fat depots and membrane phospholipids. These fatty acids are synthesized by the stearoyl-CoA desaturase. The regulation of stearoyl-CoA desaturase is therefore of considerable physiological importance and its activity is sensitive to dietary changes, hormonal imbalance, temperature changes, metals, alcohol, peroxisomal proliferators, and phenolic compounds. The *Alisma orientale* plant, or extract therefrom, is useful as an inhibitor of SCD activity which can thereby treat or reduce conditions associated with excess sebum accumulation, production, or excretion, as well as subcutaneous fat, including cellulite.

A further embodiment of the invention relates to methods of applying an effective amount of a plant, or plant extract therefrom, which inhibits adioponectin, to affected areas of the skin or hair. The plant is preferably *Alisma orientale*, and more preferably an extract of *Alisma orientale* (Sam.) Juzep. Adipocytes express a variety of proteins that function in the homeostatic control of glucose and lipid metabolism, including a 30-kDa protein known as adipocyte complement-related protein (Acrp30) or adiponectin, an adipocytokine. Secretion of adiponectin by adipocytes is enhanced by insulin stimulation, while decreased expression correlates with insulin resistance, providing support for a link between Type II diabetes and obesity (Nedvidkova J, et al. "Adiponectin, an adipocyte-derived protein" *Physiol Res.*, Nov. 15, 2004; Meier U and Gressner A M. "Endocrine regulation of energy metabolism: review of pathobiochemical and clinical chemical aspects of leptin, ghrelin, adiponectin, and resistin" *Clin Chem.* 50(9): 1511-25, 2004; Gil-Campos M, et al. "Adiponectin, the missing link in insulin resistance and obesity" *Clin Nutr.* 23(5): 963-74, 2004; all of which are incorporated herein by reference). The development of non-insulin dependent (type 2) diabetes has been suggested to be involved in dysregulation of adiponectin secretion (Putz D M, et al. "Adiponectin and C-reactive protein in obesity, type 2 diabetes, and monodrug therapy" *Metabolism* 53(11):1454-61, 2004; Gil-Campos, supra; both of which are incorporated herein by reference). In support of the link between obesity and type 2 diabetes, decreased levels of circulating adiponectin have been shown to correlate with insulin resistance and that adiponectin appears to be a potent insulin enhancer linking adipose tissue and whole-body glucose metabolism (Shetty G K, et al. "Circulating adiponectin and resistin levels in relation to metabolic factors, inflammatory markers, and vascular reactivity in diabetic patients and subjects at risk for diabetes" *Diabetes Care.* 27(10):2450-7, 2004; Schulze M B, et al. "Relationship between adiponectin and glycemic control, blood lipids, and inflammatory markers in men with type 2 diabetes" *Diabetes Care.* 27(7):1680-7, 2004; both of which are incorporated herein by reference). The *Alisma orientale* plant, or extract therefrom, is useful as an inhibitor of adiponectin production which can thereby treat or reduce conditions associated with excess sebum accumulation, production, or excretion, as well as subcutaneous fat, including cellulite.

Another embodiment of the present invention relates to a method of improving the aesthetic appearance of conditions related to skin and comprises applying to the skin, or introducing via a directed mode of delivery, a composition including one or more *Alisma orientale* components in an amount effective to improve the aesthetic appearance of conditions related to skin and associated with excess sebum production and excess accumulation or production of subcutaneous fat.

As will be appreciated by the practitioner, cosmetic treatments comprising compositions containing plant extracts, components, and/or constituents of the invention may be carried out, for example, by topically applying the cosmetic composition as described herein according to the routine technique for administering such compositions. Routine and commonly practiced techniques encompass the application of creams, lotions, gels, masks, sera, ointments, patches, make-ups, makeup-removing milks, anti-deodorants, anti-perspirants, or sunscreen compositions to the skin; spraying as a form of application is also envisioned.

EXAMPLES

The following examples describe specific aspects of the invention to illustrate the invention and provide a description of the present methods for those skilled in the art. The examples should not be construed as limiting the invention, as the examples merely provide specific methodology useful in the understanding and practice of the invention and its various aspects.

Example 1

A plant extract of the present invention may be extracted from natural raw materials by using the methods of aqueous-organic solvent extraction as is well known in the art. One such extraction process is set forth below.

Preparation of Extract

The following describes a suitable method of preparing an extract useful for preparing a composition of the present invention.

A method of preparing an extract from fresh rhizome of *Alisma orientale* was performed by first washing and drying the plant raw material. The dried plant raw material was then manually crushed and ground into a powder. The ground plant material was extracted once its weight in a 50% ethanol/water solution at 70° C. for about 30 minutes. The material remained as a liquid extraction, there was no drying of the extracted material. This liquid material may then be added to the water phase during formulation of the cosmetic product.

Example 2

Cell Culturing

A vial of cryopreserved normal human epidermal keratinocytes (Adult or Neonatal) was removed from liquid $N_2$ and placed in a 37° C. water bath for about 1-2 minutes, or until completely thawed. The vial was then removed from the water bath and the excess water was wiped off. The vial was placed into a cell culture hood for sterility. The vial was wiped with 70% ethanol to air dry for 30 seconds. While in the cell culture hood, the cells were removed from the vial and placed into a 50 ml tube. The appropriate growth media (5ml) was added drop wise while agitating the tube, allowing uniform mixture of the cells and medium while limiting cell death due to osmotic changes caused by freezing media. Medium (25 ml) was added to the 50 ml tube to bring the volume up to 30 ml. The medium/cell solution (15 ml) was added to two 75 $cm^2$ flasks, or the medium/cell solution (5 ml) was added to six 25 $cm^2$ flasks. Flasks were recapped and placed horizontally in a 37° C. humidified incubator with 5% $CO_2$ for 24 hours. After 24 hours, the old medium was aspirated and fresh room temperature growth medium (15 ml) was added onto the cells. Prior to adding the fresh growth medium, it was brought up to room temperature using a room temperature water bath without the cover. The flasks containing cells with fresh media were placed back into the 37° C. incubator. Flasks containing the old media was replaced with fresh media repeatedly until the desired confluence (75%) was reached.

Plating and Treatment

When the normal human epidermal keratinocyte cells reached the desired confluency, they were removed from the incubator and the media was aspirated off using a vacuum trap. Hank's Buffered Saline Solution (HBSS; 10 ml of 1×; Mediatech, Inc.; Herndon, Va.) was placed into the flask and the entire surface area rinsed. The HBSS was then aspirated. Trypsin (0.25% Solution; Mediatech, Inc.) was added in a 5 ml volume. The flasks were placed back into the incubator for 8 minutes. The flasks were taken from the incubator and 15 ml of Trypsin Neutralizing Solution (1×; Cascade Biologics, Inc.; Portland, Oreg.) was added to each flask to neutralize the trypsin. The medium/cell solution was removed from the flasks and placed into a 50 ml polypropylene tube. The cells were spun down using a bench top centrifuge at 1100 rpm for 6 minutes at room temperature. After spinning the cells, they were resuspended in growth medium (Basal Medium: Epilife® medium with calcium chloride (Cascade Biologics, Inc.); supplemented with 1% human keratinocyte growth factor (Cascade Biologics, Inc.); 1% Penicillin/Streptomycin (Mediatech, Inc.). The cells were resuspended by pipetting up and down. Cell culture was then placed into 100 mm tissue culture-treated plates in 10 ml volumes for incubation in a 37° C. humidified incubator with 5% $CO_2$ until 75% confluency is reached. When confluency was reached, medium was removed and replaced with fresh growth medium containing the test active at a specific concentration. Each test active was diluted in growth medium from a 10% stock vial containing a vehicle (i.e.,water, ethanol, DMSO) and the test active. Each vehicle was tested along side the test active as a control. The 100 mm tissue culture-treated plates were placed back into the 37° C. humidified incubator with 5% $CO_2$ for varying amount of times in order to establish a time course for actives being tested. The tissue culture plates were collected at 1 hour, 4 hour, 8 hour, 24 hours, and 32 hours. At each time point, the growth medium was aspirated and the cells were washed with 1× Phosphate-buffered saline. The 1× PBS was removed and the 100 mm tissue culture plates were wrapped in parafilm and stored in −80° C. until needed.

Example 3

Lipolysis Assay

Human subcutaneous pre-adipocytes (Lot # SL0024; Age 39.8 and BMI 28.69) were cultured in 96-well plates and allowed to differentiate in the absence of test compounds for about 2 weeks to confluency, i.e., until a full monolayer of cells with no plastic plate visible. The lipolysis assay screens the effects of compounds on lipolysis by measuring the amount of glycerol released into the medium. For the lipolysis assay, the culture medium was removed and the cells were gently washed 3 times with Krebs-Ringer Bicarbonate Buffer, a balanced salt solution used to maintain pH and osmotic balance, (KRB; Zen Bio, Inc.; Research Triangle Park, N.C.) at a 1× concentration. The KRB in the wells was removed and a fresh aliquot of 200 µl/well of the KRB was added. The wells were washed (once) one row at a time to ensure that the cells remained moist and stayed attached to the plate. All of the KRB was removed and the cells were treated with 150 µl/well of the controls at a or 150 µl/well of the test compounds (resuspended in KRB with 1% BSA) each at 0.1%. The assay was performed in triplicate. The plates were incubated at 37° C. for 5 hours. At the end of the treatment, 100 µl/well of the conditioned media was removed from the assay plate and added to the corresponding well of a new 96-well plate. Glycerol assay reagent (100 µl/well) was added to the new plate. The glycerol concentration was determined by GPO Trinder assay (Zen-Bio, Inc; Research Triangle Park, N.C.). The new plate was then incubated at 25° C. for 15 minutes. The optical density of each well of the new plate was measured at 540 nm.

Human subcutaneous pre-adipocytes treated with *Alisma orientale* resulted in the induction of lipolysis by about 890% when compared to the standard control (see, Table 1).

TABLE 1

|  | Lipolysis Induction | Adiponectin Inhibited | PPAR-γ Inhibited | Stearoyl CoA Desaturase Inhibited |
|---|---|---|---|---|
| *Alisma orientale* | 890% | 729% | 15-30% | 15-30% |

Example 4

Adiponectin Inhibition Assay

The effects of a test compound on adiponectin secretion were measured. Human subcutaneous adipocytes induced to produced lipids with a peroxisome proliferator-activated receptor (PPAR) gamma inducer were used for treatment (Lot # SL0024; Age 39.8 and BMI 28.69). Two concentrations of the test compounds (0.1% and 1%) were added to the cells. The secretion of adiponectin was measured after 3 days of treatment using a human adiponectin ELISA. A pair of specific antibodies directed against human adiponectin (prepared by Zen Bio, Inc.)—one immobilized on the wells for capturing the adiponectin on the test sample and another that attaches to the captured adiponectin for detection. Adiponectin present in the test sample was sandwiched between the immobilized and the secondary antibodies and was detected by first adding an anti-IgG antibody attached to horseradish peroxidase (HRP) and then adding the substrate that causes an enzymatic reaction of the HRP marked by a color change. The concentration of adiponectin is directly proportional to the color intensity measured at 450 nm. The concentrations of the samples tested were calculated using the absorbance values of the adiponectin standard solutions assayed at the same time.

*Alisma orientale* resulted in significant adiponectin inhibition when compared to standard controls. Adiponectin was inhibited by 729% in the presence of *Alisma orientale* (see, Table 1).

Example 5

PPAR-Gamma Inhibition Assay

The effects of herbal preparations on the activation of genes regulated by the peroxisome proliferator-activated gamma receptor (PPAR-gamma) receptor were measured by Azgen, LLC (Saunderstown, R.I.). Transient co-transfection assays were performed with a PPAR-gamma expression construct and a firefly luciferase reporter harboring a PPAR-gamma response element (PPARE) in CV-1 cells, derived from the kidney of a male adult African green monkey by F. C. Jensen, et al. in March, 1964. Luciferase activity was determined with a Dual-Luciferase Reporter Assay system. The firefly luminescence signal was normalized based on the background control luminescence signal and the ratio of the extract-treated wells compared to that from controls. Transfected cells were then treated with citiglizone (10 µM), a known inducer of PPAR-gamma, with or without the addition of extract. A positive response indicated the ability of active material to inhibit PPAR-gamma induction and thereby affect control of lipid production. A 50% solvent control was used in comparison.

PPAR-gamma inhibition using *Alisma orientale* was not found to be statistically significant. In the presence of *Alisma orientale*, PPAR-gamma was inhibited by about 15-30% (see, Table 1).

Example 6

Stearoyl-CoA Desaturase (SCD) Assay

The effects of herbal preparations on the inhibition of genes regulated by stearoyl-CoA desaturase (SCD) were measured by Azgen, LLC. Co-transfection assays were performed with an SCD expression construct construct and a firefly luciferase reporter harboring a SCD response element. Luciferase activity was determined with a Dual-Luciferase Reporter Assay system. The firefly luminescence signal was normalized based on the background control luminescence signal and the ratio of the herbal-treated wells over that from controls. Stearoyl CoA desaturase inhibition using *Alisma orientale* was not found to be statistically significant. *Alisma orientale* inhbted Stearoyl CoA desaturase by about 15-30% (see, Table 1).

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of ameliorating, reducing, or treating excess subcutaneous fat production, comprising topically applying to a subject in need thereof, a topical composition consisting essentially of:

a cosmetically, dermatologically, pharmaceutically, or physiologically effective amount of *Alisma orientate* or an extract thereof sufficient to reduce a condition selected from the group consisting of excess subcutaneous fat, upregulation of PPAR receptors, upregulation of stearoyl CoA desaturase, upregulation of adiponectin production, and/or any combinations thereof, and a cosmetically, dermatologically, pharmaceutically, or physiologically acceptable vehicle;

wherein the topical composition is applied in an amount effective to ameliorate, reduce, or treat excess fat production in an area of non-diseased skin, thereby improving the skin's aesthetic appearance.

2. The method according to claim 1, wherein the extract is derived from a rhizome of an *Alisma orientale* (Sam.) Juzep plant.

3. The method according to claim 1, wherein said composition is applied for a period of time effective to ameliorate, reduce, and/or treat excess subcutaneous fat production.

4. The method according to claim 1, wherein the composition is applied by daily topical application for at least one week.

5. The method according to claim 1, wherein the plant extract is present in an amount of about 0.0001 weight % to about 50 weight % based on the total weight of the composition.

6. The method according to claim 1, wherein the plant extract is present in an amount of about 0.001 weight % to about 20 weight % based on the total weight of the composition.

7. The method according to claim 1, wherein said composition is applied to an area of skin in need thereof, in an amount sufficient to improve the condition and/or aesthetic appearance of the skin, and wherein the condition is cellulite.

* * * * *